(12) United States Patent
Bajpai et al.

(10) Patent No.: US 9,718,855 B2
(45) Date of Patent: Aug. 1, 2017

(54) NUCLEOSIDES AND OLIGONUCLEOTIDES FOR STUDIES ON REVERSAL OF CYTOTOXIC AND MUTAGENIC DAMAGE OF DNA AND AS DIAGNOSTICS TOOLS

(71) Applicant: ChemGenes Corporation, Wilmington, MA (US)

(72) Inventors: Satya P. Bajpai, Lucknow (IN); Sant K Srivastav, Burlington, MA (US); Suresh C. Srivastava, Burlington, MA (US)

(73) Assignee: ChemGenes Corporation, Wilmington, MA (US)

( * ) Notice: Subject to any disclaimer, the term of this patent is extended or adjusted under 35 U.S.C. 154(b) by 0 days.

(21) Appl. No.: 14/185,907

(22) Filed: Feb. 20, 2014

(65) Prior Publication Data
US 2014/0350234 A1 Nov. 27, 2014

Related U.S. Application Data

(63) Continuation of application No. 11/018,567, filed on Dec. 20, 2004, now Pat. No. 8,785,619.

(51) Int. Cl.
*C07H 19/06* (2006.01)
*C07H 19/16* (2006.01)
*C07H 21/00* (2006.01)

(52) U.S. Cl.
CPC ............ *C07H 21/00* (2013.01); *C07H 19/06* (2013.01); *C07H 19/16* (2013.01); *Y02P 20/55* (2015.11)

(58) Field of Classification Search
CPC ................................................ A23V 2300/10
See application file for complete search history.

(56) References Cited

U.S. PATENT DOCUMENTS

| | | |
|---|---|---|
| 6,610,842 B1 | 8/2003 | Ravikumar et al. |
| 8,309,707 B2 | 11/2012 | Srivastava et al. |
| 8,541,569 B2 | 9/2013 | Srivastava et al. |
| 2002/0150936 A1 | 10/2002 | Beigelman et al. |

OTHER PUBLICATIONS

Trewick, S.C., Henshaw, T.F., Hausinger, R.P., Lindahl, T., Sedgwick, B. (2002) Oxidative demethylation by *Escherichia coli* AlkB directly reverts DNA base damage. Nature, vol. 419, p. 174-178.*

Mizuno, H., Okuyama, H., Hayatsu, H., Ukita, T. (1964) Modifications of Nucleosides and Nucleotides. II. Reaction of Ethylene Oxide with 1-Methylcytosine, Chemical and Pharmaceutical Bulletin, vol. 12, No. 10, p. 1240-1246.*

Communication from U.S. Patent & Trademark Office, Final Office Action dated Jan. 16, 2014 in Copending U.S. Appl. No. 13/633,857.

Communication from U.S. Patent & Trademark Office, Advisory Action dated Dec. 13, 2013 in Copending U.S. Appl. No. 13/138,465.

Communication from U.S. Patent & Trademark Office, Final Office Action dated Jul. 2, 2013 in Copending U.S. Appl. No. 13/138,465.

Mikhailov, S.N. et al. "Chemical incorporation of 1-methyladenosine into oligonucleotides", Nucleic Acids Research, 2002, vol. 30, No. 5, pp. 1124-1131, Oxford University Press.

Froehler B.C. et al. "Dialkylformamidines: depurination resistant N6-protecting group for deoxyadenosine", Nucleic Acids Research, 1983, vol. 11, No. 22, pp. 8031-8036, IRL Press Limited, Oxford, England.

Schulhof, J.C. et al. "Facile removal of new base protecting groups useful in oligonucleotide synthesis", Tetrahedron Letters, 1987, vol. 28, No. 1, pp. 51-54, Pergamon Journals Ltd.

Schwartz, M.E. et al. "A universal adapter for chemical synthesis of DNA or RNA on any single type of solid support", Tetrahedron Letters, 1995, vol. 36, No. 1, pp. 27-30, Elsevier Science Ltd.

Ravikumar, V.T. et al. "Stereoselective synthesis of alkylphosphonates: a facile rearrangement of cyanoethyl-protected nucleoside phosphoramidites", Organic Process Research and Development, 2004, vol. 8, pp. 603-608, American Chemical Society.

* cited by examiner

*Primary Examiner* — Layla Berry
(74) *Attorney, Agent, or Firm* — Harvest IP Law LLP

(57) ABSTRACT

The present invention is directed to n-alkylated synthetic nucleosides of high regiospecific purity and oligonucleotides that can be utilized for studies on reversal of cytotoxic and mutagenic DNA damage, and as diagnostic tools.

1 Claim, 14 Drawing Sheets

UV Analysis
NAME: 5'-DMT-$N^3$ Ethyl-deoxy Cytidine (n-bz)  Figure # 1
Catalog #: Custom
Lot #: IP89-6
F.W.: 659.66
Date: 12/03/2002
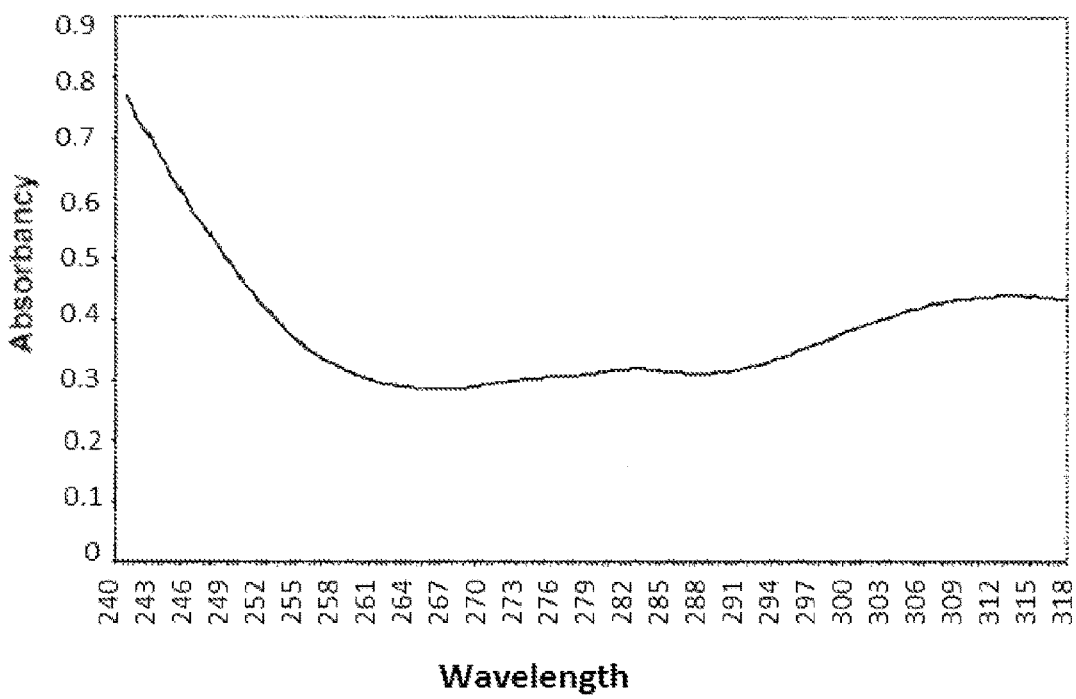
Optical Density Ratios:
  250/260 nm: 1.529
  260/280 nm: 0.984
$E_{max}$ at 250 nm = 13,721     Solvent: Methanol Date: Tue, Dec 3, 2002 5:38 PM
Data: DMT-N3Ethyl-dbzC/IP89-6-001   Figure # 2
Sample:   Mobile Phase #ACN : 0.1M TEAA(pH 7.0) [95:5] using C-18. [Isocratic system]
Lot No # IP89-6
Dissolved in : ACN
Flow rate : 1.5 ml/min
Method: Method-02-Amidite
Sampling Int: 0.1 Seconds
Data:
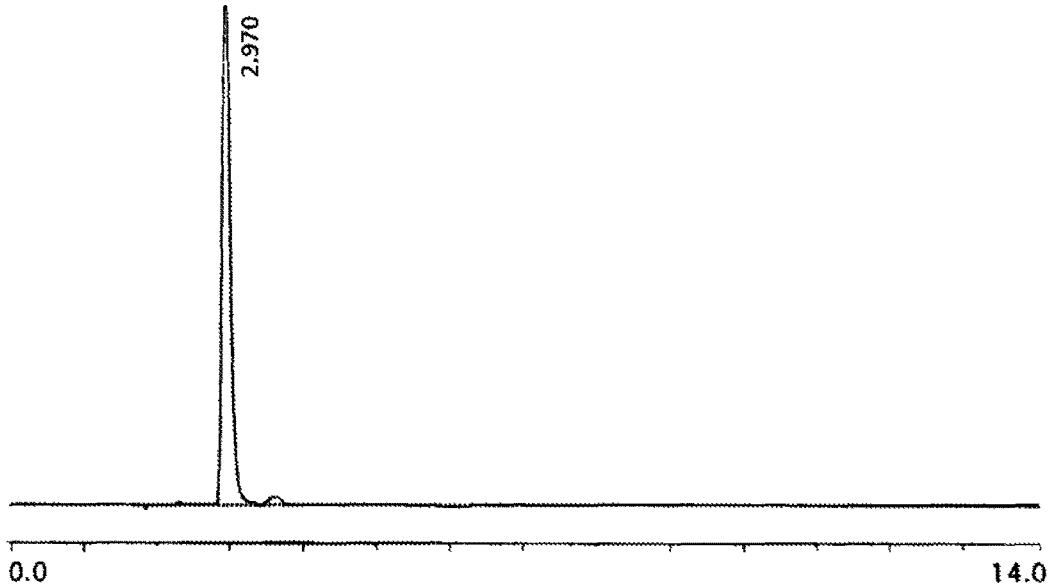
| Analysis: | Channel A | | | | |
|---|---|---|---|---|---|
| Peak No. | Time | Type | Height($\mu$V) | Area($\mu$V-sec) | Area% |
|  | 1.796 | N1 | 103 | 207 | 0.070 |
|  | 1.925 | N2 | 71 | 316 | 0.107 |
|  | 2.318 | N3 | 152 | 1868 | 0.634 |
| 1 | 2.970 | N4 | 40157 | 283533 | 96.356 |
|  | 3.646 | N5 | 684 | 7026 | 2.387 |
|  | 5.600 | N1 | 77 | 550 | 0.186 |
|  | 6.786 | X2 | 26 | 755 | 0.256 |
| Total Area |  |  |  | 294255 | 99.996 |

Date: Tue, Dec 3, 2002 ·5:02PM
Data: DMT-N3Ethyl-dbzC-OP/IP98··001     Figure #3
Sample:     Mobile Phase #ACN : 0.1M TEAA (pH 7.0) [95:5] using C-1 8.
            [Isocratic system]
            LotNo#IP98-6
            Dissolved in :ACN
            Flow rate: 1.5 ml/min
Processing File:
Method: Method-02-Amidite
Sampling Int: 0.1 Seconds
Data:
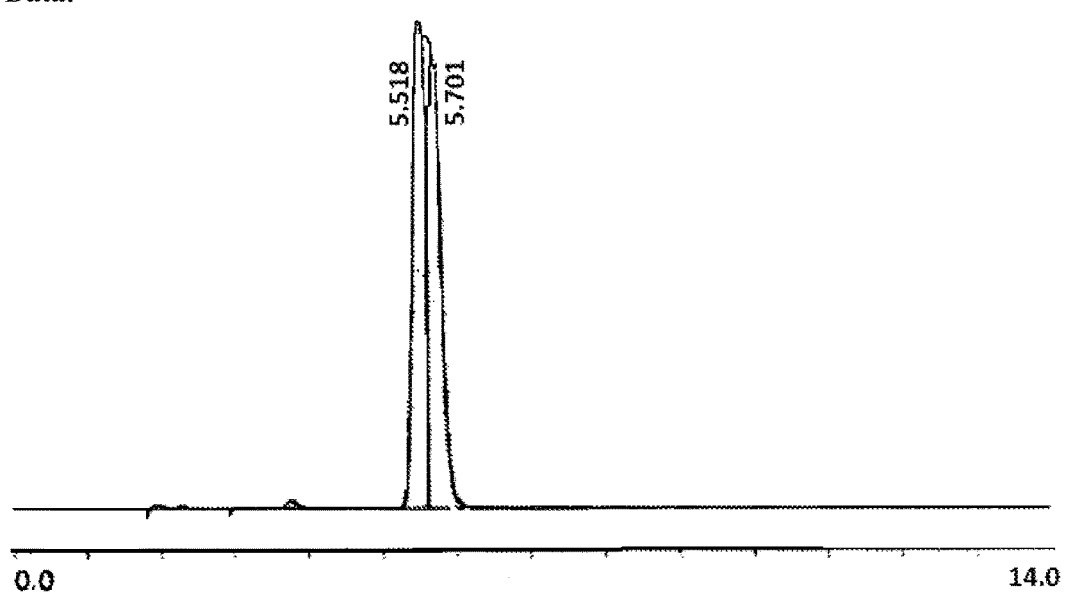
| Analysis: | Channel A | | | | |
|---|---|---|---|---|---|
| Peak No. | Time | Type | Height($\mu$V) | Area($\mu$V-sec) | Area% |
|  | 1.793 | N1 | 119 | 405 | 0.048 |
|  | 1.963 | N2 | 317 | 2378 | 0.285 |
|  | 2.170 | N3 | 148 | 1009 | 0.121 |
|  | 3.775 | N4 | 613 | 7465 | 0.896 |
|  | 4.226 | N5 | 96 | 2201 | 0.264 |
| 1 | 5.518 | N1 | 37313 | 386358 | 46.385 |
| 2 | 5.701 | N2 | 35323 | 419526 | 50.367 |
|  | 7.171 | N3 | 252 | 7268 | 0.872 |
|  | 7.613 | N4 | 227 | 4354 | 0.522 |
|  | 8.145 | N5 | 114 | 1970 | 0.236 |
| Total Area |  |  |  | 832934 | 99.996 |

UV Analysis
NAME: 5'-DMT-$N^3$ Ethyl-deoxy Cytidine (n-bz) phosphoramidite     Figure # 4
Catalog #: Custom
Lot #: IP102-6
F.W.: 861.96
Date: 12/18/2002
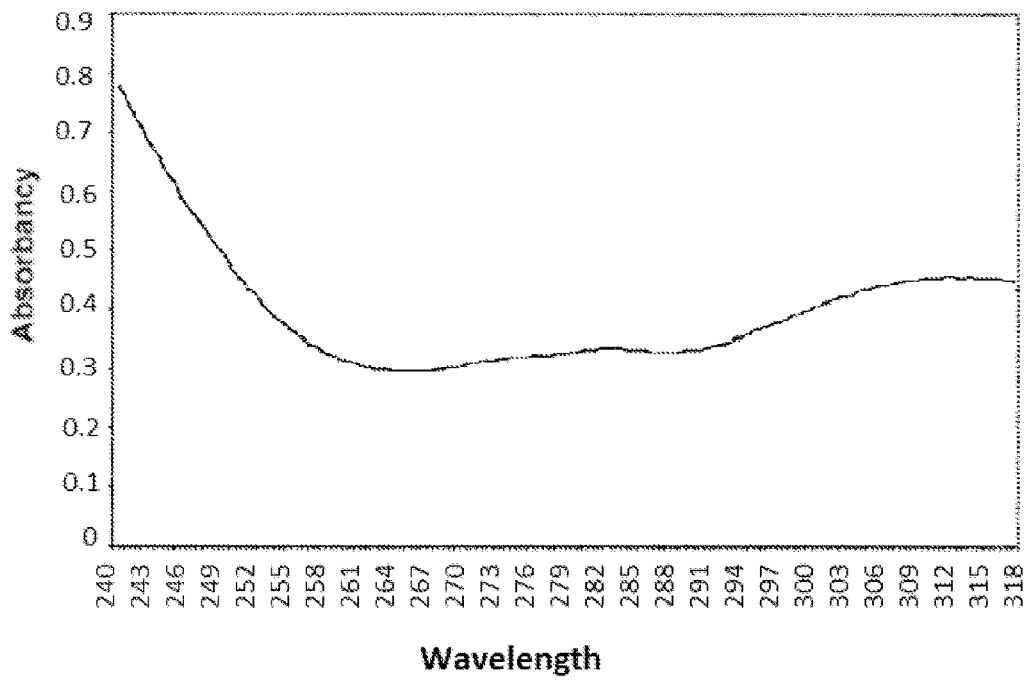
Optical Density Ratios:
  250/260 nm: 1.505
  260/280 nm: 0.960
$E_{max}$ at 250 nm = 16,343     Solvent: Methanol Date: Fri, Dec 6, 2002 5:34 PM
Data: DMT-N'CH3-N6PACdA/IP106-6-002
Figure # 5
Sample: Mobile Phase #ACN : 0.1M TEAA(pH 7.0) [60:40] using C-18. [Isocratic system]
Lot No # IP106-6A
Dissolved in : ACN
Flow rate : 1.5 ml/min
Method: Method-03-DMT-N-Prot
Sampling Int: 0.1 Seconds
Data:
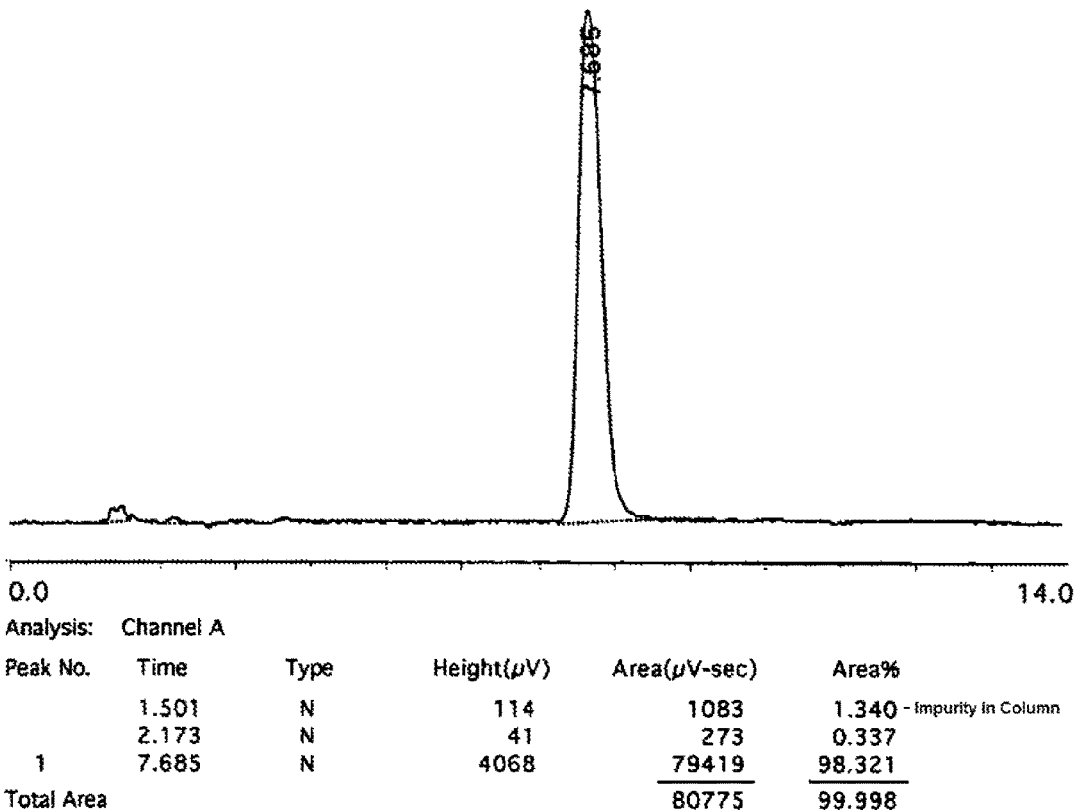
| Analysis: | Channel A | | | | |
|---|---|---|---|---|---|
| Peak No. | Time | Type | Height(μV) | Area(μV-sec) | Area% |
| | 1.501 | N | 114 | 1083 | 1.340 - Impurity in Column |
| | 2.173 | N | 41 | 273 | 0.337 |
| 1 | 7.685 | N | 4068 | 79419 | 98.321 |
| Total Area | | | | 80775 | 99.998 |

Date: Wed, Dec 18, 2002 2:18PM
Data: DMT-N$^1$-CH3-N6PAC-dA-OP/IP1-001         Figure # 6
Sample:  Mobile Phase # ACN: 0.1M TEAA (pH 7.0) [95:5] Using C-18, [isocratic System]
    Lot#: IP114-6
    Dissolved in: ACN
    Flow rate: 1.5 ml/min
Processing File:
Method: Method-02-Amidite
Sampling Int: 0.1Seconds
Data:
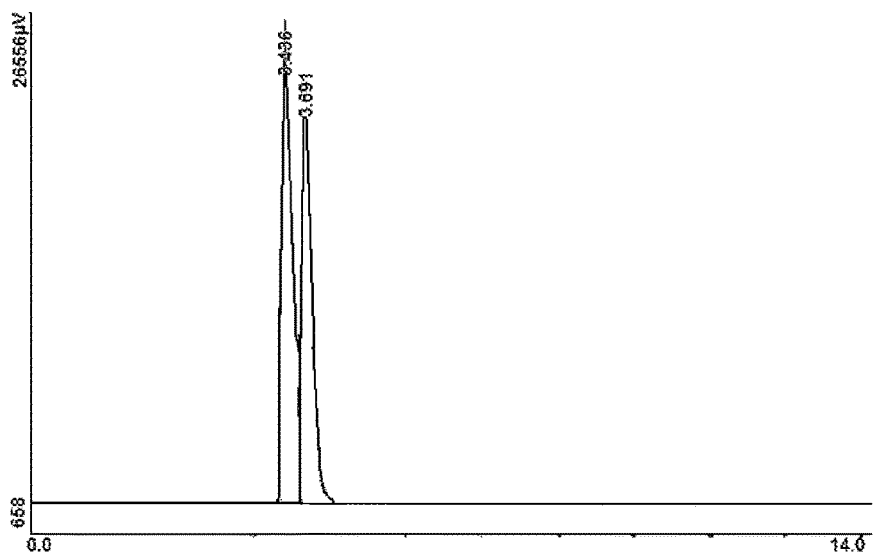
| Analysis | Channel A | | | | |
|---|---|---|---|---|---|
| Peak No. | Time | Type | Height(μV) | Area(μv-sec) | Area (%) |
|  | 1.760 | N1 | 139 | 234 | 0.061 |
|  | 2.241 | N2 | 69 | 941 | 0.246 |
|  | 2.695 | N3 | 61 | 361 | 0.094 |
|  | 3.118 | N4 | 90 | 1241 | 0.324 |
| 1 | 3.436 | N5 | 25663 | 199662 | 52215 |
| 2 | 3.691 | N6 | 20324 | 179939 | 47.057 |
| Total Area | | | | 382378 | 99.997 |

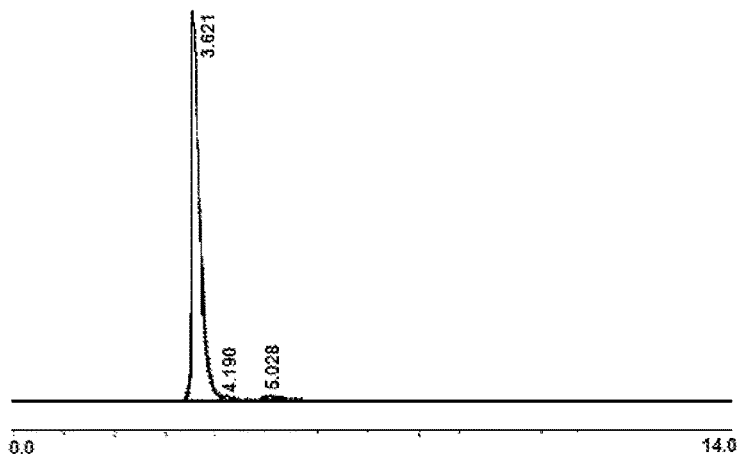
Figure # 7

Date: Wed, Feb 5, 2003 6:03 PM
Data: DMT-N'CH3-dA+DMT-N6CH3-dA-001     Figure # 8
Sample:   Mobile Phase #ACN : 0.1M TEAA(pH 7.0) [60:40] using C-18. [Isocratic system]
          Lot No # DMT-N'CH3-dA with DMT-N6CH3-dA(Co-inject)
          Dissolved in : ACN
          Flow rate : 1.5 ml/min
Processing File:
Method: Method-07-DMT-N-Prot(Iso)
Inject Vol: 8
Sampling Int: 0.1 Seconds
Data:
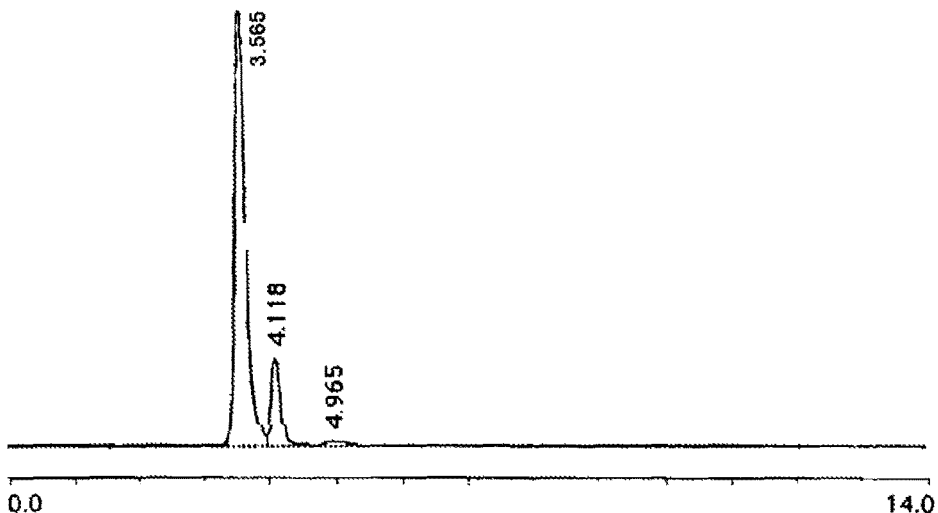
Analysis:   Channel A
| Peak No. | Time | Type | Height(µV) | Area(µV-sec) | Area% |
|---|---|---|---|---|---|
|   | 1.525 | N1 | 166 | 1004 | 0.131 |
|   | 1.636 | N2 | 67 | 264 | 0.034 |
|   | 2.173 | N1 | 119 | 404 | 0.052 |
|   | 2.616 | N2 | 55 | 459 | 0.059 |
| 1 | 3.565 | N1 | 64397 | 617557 | 80.667 |
| 2 | 4.118 | N2 | 13098 | 119817 | 15.650 |
| 3 | 4.965 | N3 | 967 | 22452 | 2.932 |
|   | 7.120 | N | 176 | 1576 | 0.205 |
|   | 10.765 | N | 100 | 1485 | 0.193 |
|   | 11.818 | N | 42 | 542 | 0.070 |
| Total Area |   |   |   | 765560 | 99.993 |

UV Analysis
NAME: $N^1$ Methyl-$N^2$ DMF-deoxy Guanosine      Figure # 9
Catalog #: Custom
Lot #: IP68-6
F.W.: 336.26
Date: 12/03/2002
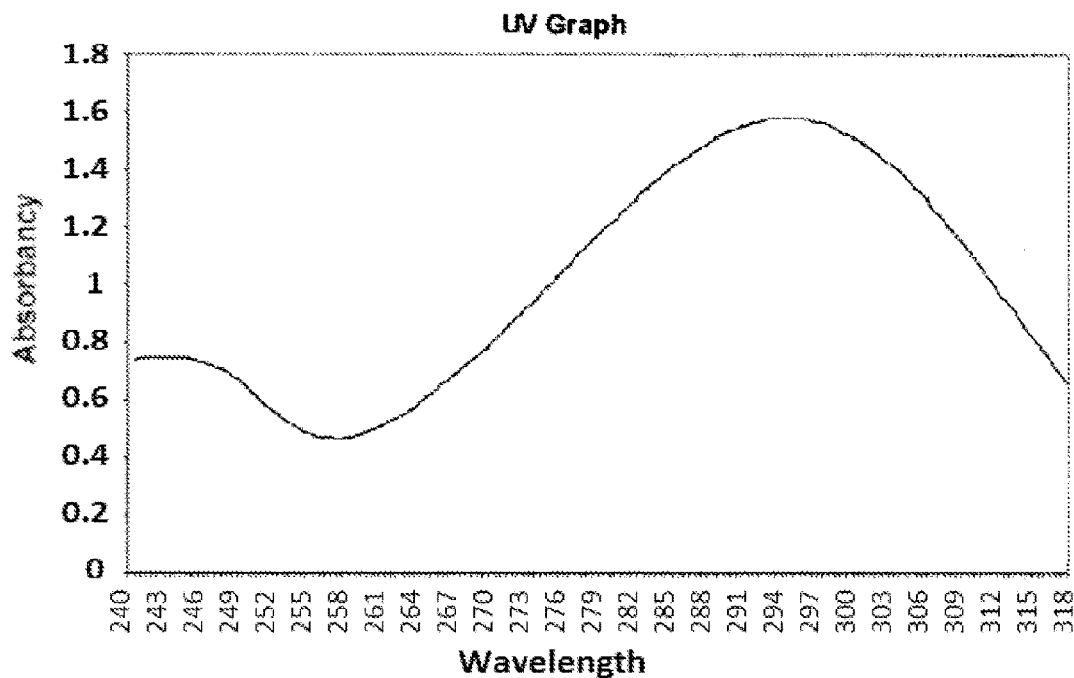
Optical Density Ratios:
    250/260 nm: 1.289
    260/280 nm: 0.412
$E_{max}$ at 296 nm = 21,265      Solvent: 0.2N HCl Date: Tue, Dec 3, 2002 3:13 PM
Data: N'Methyl-N2DMF-dG/IP68-6-004    Figure #10
Sample:   Mobile Phase #ACN : 0.1M TEAA(pH 7.0) [20:80] using C-18. [Isocratic system]
Lot No # IP68-6
Dissolved in : .2N.HCL
Flow rate : 1.5 ml/min
Method: Method-04-Nucleoside
Sampling Int: 0.1 Seconds
Data:
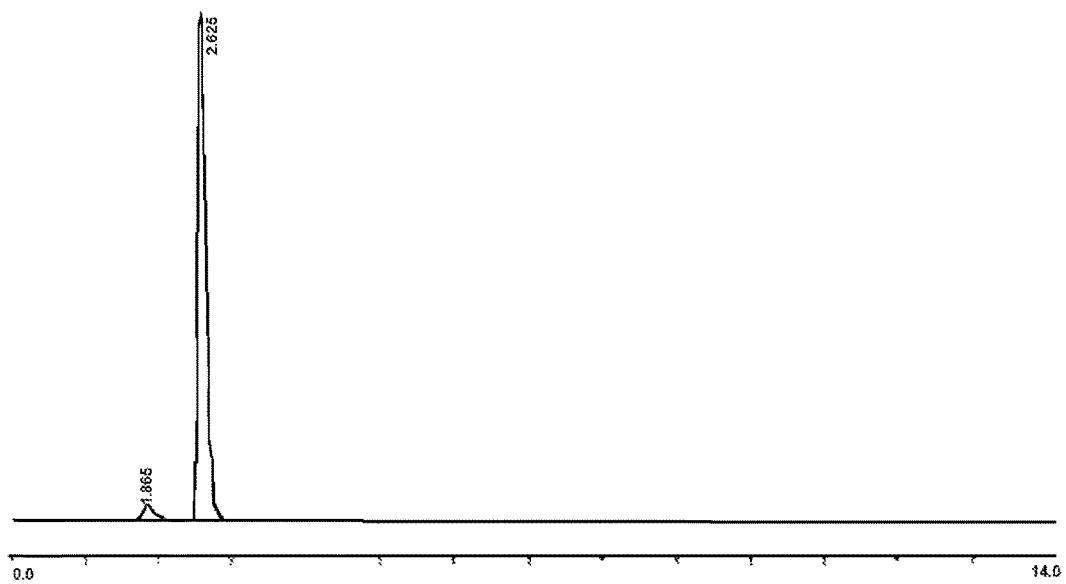
Analysis     Channel A
| Peak No. | Time | Type | Height(μV) | Area(μv-sec) | Area (%) |
|---|---|---|---|---|---|
| 1 | 1.865 | N1 | 2312 | 21483 | 3.963 |
|   | 2.355 | N2 | 50 | 14 | 0.002 |
| 2 | 2.625 | N3 | 73605 | 520465 | 96.033 |
| Total Area |  |  |  | 541962 | 99.998 |

NAME: 5'-DMT-N$^1$ Methyl-N$^2$ DMF-deoxy Guanosine    Figure # 11
Catalog #: Custom
Lot #: IP87-6
F.W.: 638.59
Date: 12/03/2002
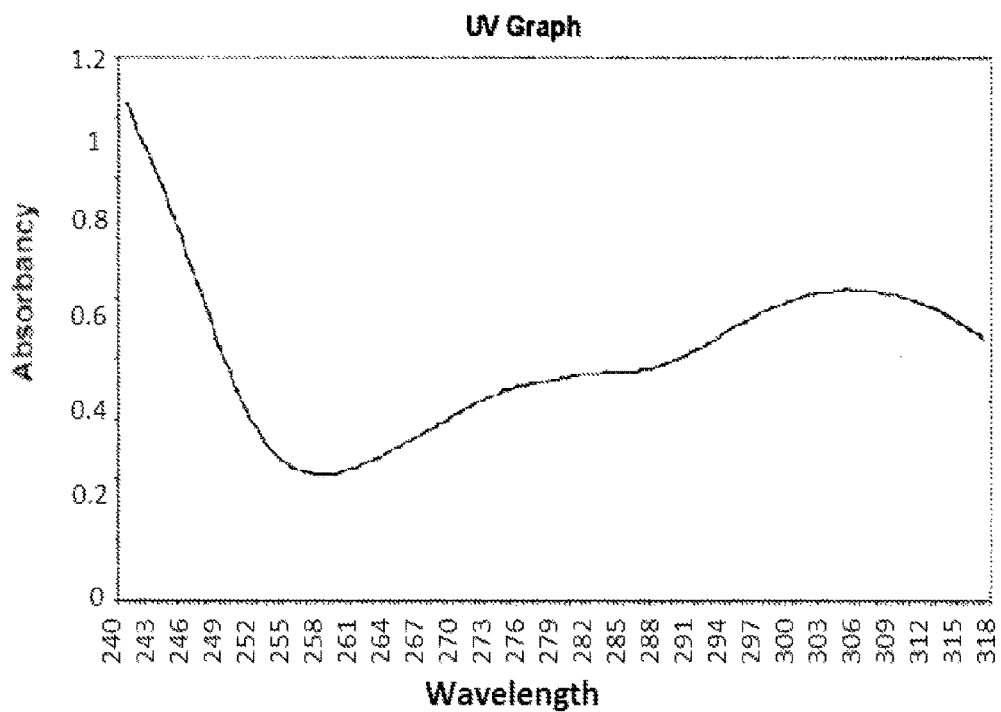
Optical Density Ratios:
    250/260 nm: 1.678
    260/280 nm: 0.584
$E_{max}$ at 307 nm = 17,676    Solvent: Methanol Date: Wed, Nov 27, 2002 1:54 PM
Data: DMT-N'CH3-N2DMF-dG/IP81-6-002   Figure # 12
Sample:   Mobile Phase #ACN : 0.1M TEAA(pH 7.0) [60:40] using C-18. [Isocratic system]
Lot No # IP81-6
Dissolved in : ACN
Flow rate : 1.5 ml/min
Method: Method-03-DMT-N-Prot
Sampling Int: 0.1 Seconds
Data:
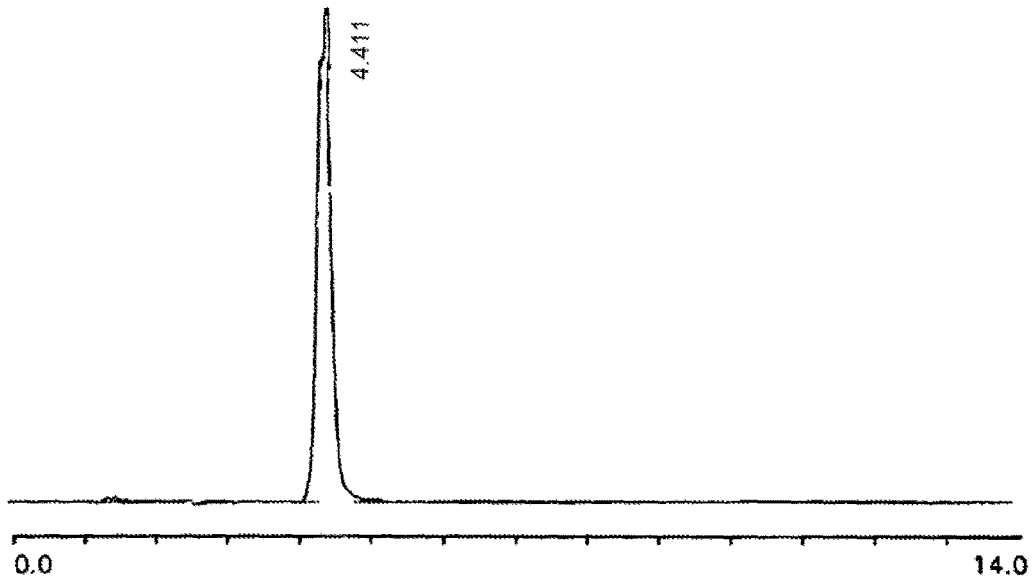
Analysis:   Channel A
| Peak No. | Time | Type | Height($\mu$V) | Area($\mu$V-sec) | Area% |
|---|---|---|---|---|---|
|  | 1.398 | N | 183 | 2107 | 0.986 |
| 1 | 4.411 | N | 17920 | 211461 | 99.013 |
| Total Area |  |  |  | 213568 | 99.999 |

UV Analysis
NAME: 5'-DMT-$N^1$ Methyl-$N^2$ DMF-deoxy Guanosine phosphoramidite   Figure # 13
Catalog #: Custom
Lot #: IP126-6
F.W.: 838.69
Date: 12/23/2002
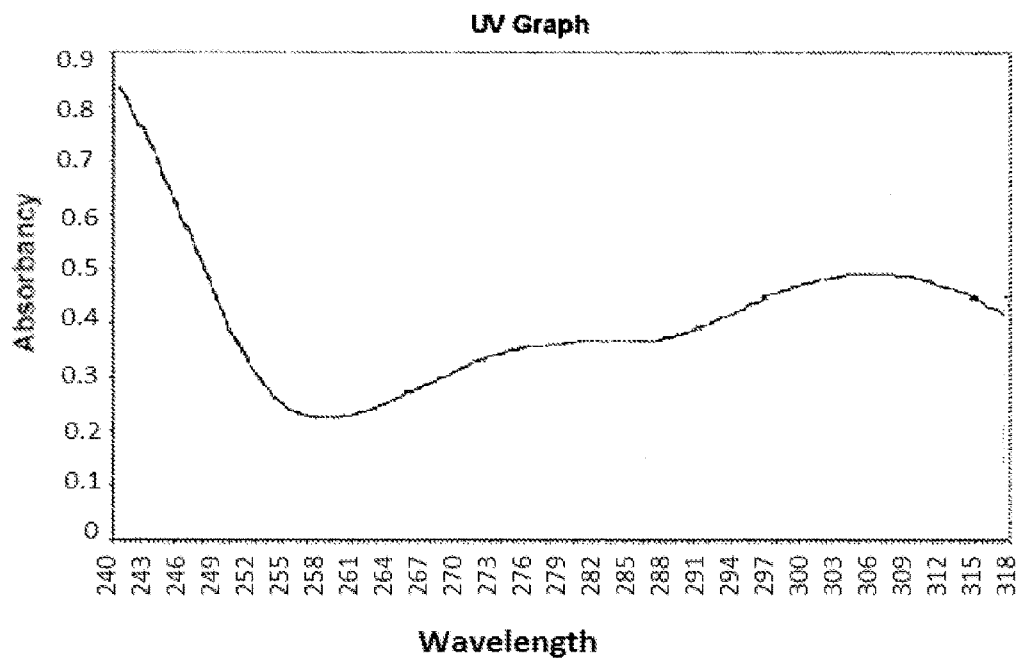
Optical Density Ratios:
  250/260 nm: 1.738
  260/280 nm: 0.617
$E_{max}$ at 307 nm = 16,371    Solvent: Methanol Date: Mon, Dec 23, 2002 5:38 PM
Data: DMT-N'CH3-N2DMF-dG-OP/IP1-003    Figure # 14
Sample:   Mobile Phase #ACN : 0.1M TEAA(pH 7.0) [90:10] using C-18. [Isocratic system]
Lot No # IP126-6
Dissolved in : ACN
Flow rate : 1.5 ml/min
Method: Method-02-Amidite
Sampling Int: 0.1 Seconds
Data:
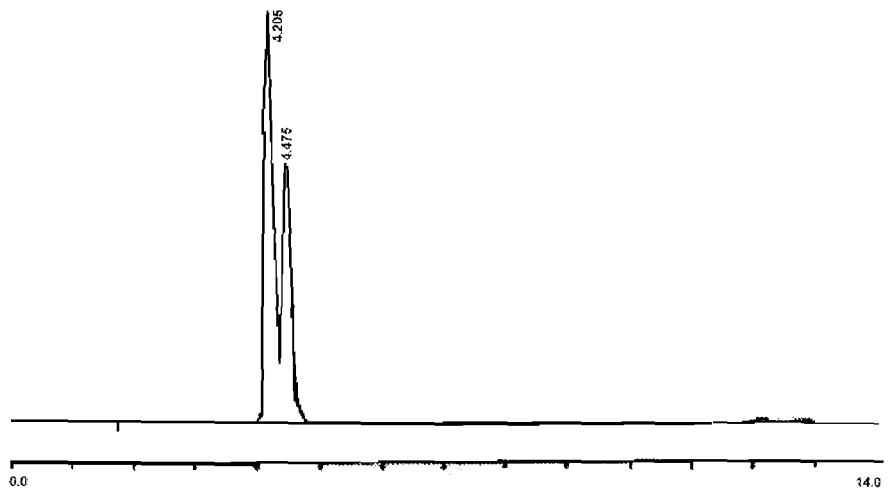
| Analysis | Channel A | | | | |
|---|---|---|---|---|---|
| Peak No. | Time | Type | Height(μV) | Area(μv-sec) | Area (%) |
|  | 1.723 | N1 | 272 | 735 | 0.242 |
|  | 1.823 | N2 | 56 | 8 | 0.002 |
|  | 2.218 | N3 | 56 | 235 | 0.077 |
|  | 2.973 | N1 | 119 | 1092 | 0.359 |
|  | 3.431 | N2 | 136 | 985 | 0.324 |
| 1 | 4.205 | N1 | 20709 | 165880 | 54.625 |
| 2 | 4.475 | N2 | 13821 | 124381 | 40.959 |
|  | 12.123 | N1 | 287 | 6172 | 2.032 |
|  | 12.823 | N2 | 210 | 4179 | 1.376 |
| Total Area |  |  |  | 303667 | 99.996 |

NUCLEOSIDES AND OLIGONUCLEOTIDES FOR STUDIES ON REVERSAL OF CYTOTOXIC AND MUTAGENIC DAMAGE OF DNA AND AS DIAGNOSTICS TOOLS

CROSS-REFERENCE TO OTHER APPLICATION

This application is a continuation application to U.S. application Ser. No. 11/018,567, now U.S. Pat. No. 8,785,619, filed Dec. 20, 2004, which in turn claims priority to U.S. Provisional Application Ser. No. 60/531,237, filed Dec. 20, 2003. The entire teachings of the above applications are incorporated herein by reference.

FIELD OF THE INVENTION

This invention relates to n-alkylated synthetic nucleosides and phosphoramidites of high regio-specific purity and stability and selective deprotection for high purity n-alkylated DNA and RNA synthesis useful for study of mechanism of cytotoxic and mutagenic DNA damage that occurs from the incorporation of methylated nucleosides, the corresponding phosphates and triphosphates and their precursors, via de novo DNA synthesis. The phosphoramidites of the synthetic alkylated nucleosides have been developed to synthesize sequence specific oligonucleotides and subsequent studies on reversal of cellular cytotoxic and mutagenic damages, in terms of presence of in vivo capability to detect the cellular capabilities for reversal of potential mutagenic and cytotoxic damages. The reagents thus could be extremely valuable tools as diagnostics reagents for cellular capability of reversal of cellular mutagenic and cytotoxic damages.

BACKGROUND OF THE INVENTION

Alkylation of DNA presents an important event of far reaching biological consequences. DNA alkylating agents are present endogenously, found in the environment, and are used in chemotherapy. Human beings are constantly exposed to alkylating agents from a wide variety of sources. For a better understanding of the changes at gene level responsible for DNA damage and a timely intervention in the DNA damaging process, availability of critical nucleosides, DNA and RNA to study the mechanism of DNA damage and repair is required. The information thus generated would have vast implication on understanding of various diseases that are the direct result of DNA damage from alkylation. Since all the alkylation and resulting mutation involve changes at gene level, the control of such damages at the gene level is an ideal approach.

Efforts are needed towards identification of alkylating agents, development of nucleosides and oligonucleotides which are suitable to synthesize alkylated DNA and RNA oligonucleotides, valuable in the study of optimum structural parameters for the reversal of cytotoxic DNA and RNA produced endogenously. This is essential, since application of the reversal process at early stages when mutation is at the beginning stage will help effective control of lesions that are at benign stages of toxic development.

The two main places of alkylation of DNA are O-alkylation and N-alkylation. Alkylation of DNA may lead to cytotoxic and mutagenic damage of the gene and gene products. However, the extent of damage depends upon the site of alkylation as well as on the nature of the base. N-Methylation of guanine occurs mainly at $N^7$ position. However, this alkylation does not interfere with its pairing with cytosine and is therefore, harmless. The glycosidic bond of $N^7$-methyl G undergoes slow and spontaneous hydrolysis creating a apurinic site which is a target for repair. On the other hand, $N^7$-alkylation of G with a bifunctional agent such as nitrogen mustard causes cross-linking of two neighboring guanines leading to cell toxicity.

In the mono alkylation of adenine, the alkyl group at $N^3$ occupies minor grove of the DNA double helix causing interference to DNA polymerase activity thus resulting in a major toxic lesion.

3-Alkyl guanines behave in a similar fashion as 3-alkyl adenines. However, formation of 3-alkyl guanines is much less prevalent (~10 fold less) and therefore, of lesser significance. $N^1$-alkylation of adenine interferes with A-T pairing. However, this lesion gets slowly excised in vivo.

O-Alkylation of the DNA bass fixes them in their enolic forms that may influence their base pairing. Thus, O6-methyl guanine forms an $O^6$ Me G-C base pair that is more stable in a DNA duplex than O6-Me G-T base mispair. However, DNA polymerase activity shows preference for incorporation of Ton replication. The enolic forms of $O^4$-methyl thymine and O4-ethyl thymine form base mispair with G that undergoes replication of a defined DNA sequence. However, alkyl pyrimidines are very minor products of DNA alkylation and are therefore, of low significance towards biological effects.

O-Alkylation of the phosphate residue in DNA results in the formation of a triester. Such triesters are repairable and do not seem to be important in inducing cell toxicity or mutagenic activity.

Therefore, from the above discussion it is clear that alkylation of DNA may cause cytotoxic and mutagenic damage depending upon the site of alkylation. This may have serious consequences in the formation of Gene and Gene products. In nature human beings are constantly exposed to alkylating agents from a wide variety of sources as mentioned above. Repair of the damaged DNA is therefore essential for normal activity. All living cells possess various DNA repair enzymes. These are more predominant in humans as compared to rodents. Under the influence of alkylating agents, E. coli respond by inducing the expression of four genes, ada, alkA, aidB, and alkB. The ada protein is an $O^6$-methyl guanine-DNA methyltransferase and also regulates this adaptive response. AlkA is a 3-methyl adenine-DNA glycosylase, and aidB is meant to destroy certain alkylating agents. AlkB was isolated in 1983 by Kataoka et. al (Kataoka, H, Yamamoto, Y, & Sekiguchi, M., J. Bacteriol. 153, 1301-1307, 1983) but its exact role is still not clear. It has been shown to protect human cells against alkylation induced toxicity (Chen, B. J., Carroll, P., & Sanson, L., J. Bacteriol 176, 6255-6261, 1994). It processes the cytotoxic DNA damage generated in single-stranded DNA by SN2 methylating agents such as MeI, dimethylsulphate, methyl methanesulphonate etc. (Dinglay, S., Trewick, S. C., Lindahl, T., & Sedgwick, B., Genes Dev 14, 2097-2105, 2000). Its role in oxidative demethylation identified recently, is discussed under direct reversal of alkylated DNA. In a recent study it has been demonstrated that AlkB suppresses both genotoxicity and Mutagenesis at low doses of 1-alkylpurine and 3-alkylpyrimidine DNA damages in vivo (J. C. Delany and J. M. Essigmann, PNAS, USA, 101, 39, 14051-14056, 2004). Similarly it has been shown that $N^3$-methylthymidine containing oligonucleotides could be repaired by AlkB in vitro (P. Koivisto, P. Robins, T. Lindahl, B. Sidgwick, J. Biol. Chem., 10, 1074, 2004).

There are two types of DNA repair mechanisms that operate in living cells: i) excision repair of altered residues and ii) direct reversal of modified DNA.

Excision repair is the most common mechanism that operates in mammalian cells for DNA repair. There are two types of excision repair: a) nucleotide excision and b) base excision. Both are error free mechanisms. In the nucleotide excision repair, an endonuclease initiates the process by making an excision on the single strand on either side of the lesion of the damaged nucleotide some 12 base apart. The excised nucleotide containing the lesion is released by DNA helicase B while it is still bound to the protein complex. The gap thus created on the single strand is filled up by DNA polymerase I that binds and fills the gap and subsequently the ligation is completed.

In base excision, the enzyme DNA glycosylase hydrolyses the glycosidic bond of modified purine or pyrimidine nucleosides. Thus, the enzyme 3-methyl adenine-DNA glycosylase acts on 3-methyl adenine. The next step is incision of the phosphate backbone by an AP endonuclease followed by exonuclease action which excises the nucleoside creating a gap on the single strand. Filling of the gap by DNA polymerase I followed by ligation as mentioned for nucleotide excision process, completes the repair process.

Direct reversal of damaged DNA also occurs under the influence of certain enzymes. Thus, O-demethylation in $O^6$-methyl guanine is effected by the enzyme O6-methylguanine DNA methyltransferase. The SH group of Pro-Cys-His sequence of the enzyme near its C terminus, acts as a methyl acceptor, thus converting O-Me to OH. The same enzyme can also dealkylate ethyl, 2-hydroxyethyl, and 2-chloroethyl $O^6$-derivatives of guanine

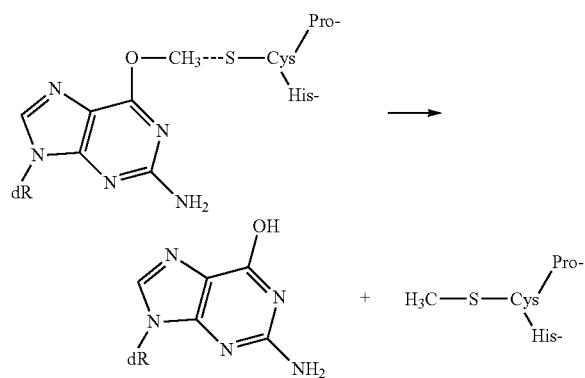

N-dealkylation is effected by alkB protein. Recently it has been shown by two independent groups (Faines, P. O., Johanson, R. F., & Seeberg, E., Nature, 419, 178, 2002; Trewick, S. C., Henshaw, T. F., Hausinger, R. P., Lindahl, T., & Sedgwick, B., Nature, 419, 174-178, 2002) that alkB resembles the Fe(ll)- and α-ketoglutarate-dependent dioxygenase. The enzyme couples oxidative decarboxylation of α-ketoglutarate to the hydroxylation of methylated bases in DNA, resulting in the reversal to unmodified base and release of formaldehyde as shown below:

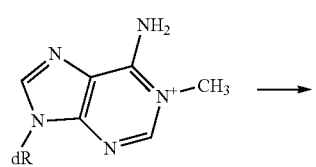

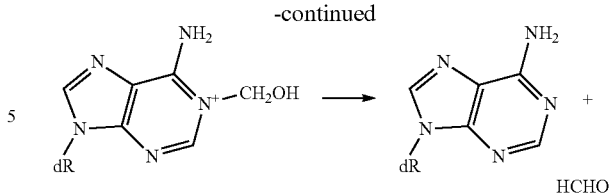

Modified nucleosides and nucleotides find application in various chemical and biological studies. Such modifications have been linked to control of gene expression at both the levels of transcription and translation. For these studies, purified preparations of alkylated nucleosides and nucleotides are required. A large number of N-methyl purines have been isolated from various biological sources and identified (Jones, J. W., Robins, R. K., J. Am. Chem. Soc, 84, 1914, 1962).

Alkylation of various unprotected derivatives of guanine led to a mixture of products. alkylated at $N^1$, N, $N^7$, or $O^6$ positions (Kamimura, T., Tsuchiya, M., Urakani, K. l., Kaura, K., Sekine, M., J. Am. Chem. Soc. 106, 4552-4557, 1984).

Extensive work has also been reported on synthetic approach to alkylated nucleosides and nucleotides. Bredreck and Martini (Bredereck, H., and Martini, A., Ber, 80, 401, 1948) treated triacetyl guanosine with excess diazomethane to obtain 1-methyl guanosine. However, the product was later shown to be 7-methyl guanosine (Jones, J. W., and Robins, R. K., J. Am. Chem. Soc. 85, 193-201, 1963). Methylation at pH 13-14 with dimethylsulphate in the presence of alkali gave a mixture of 7-methyl guanosine with methylation occurring at ribose unit as well. $O^6$-Alkylation of guanosine has also been reported (Ramaswamy, K. S., Bakir, F., Baker, B., Cook, P. D., J. Heterocycl. Chem. 30, 1373-1378, 1993). Regioselective alkylation at N' position of guanosine was achieved by Vincent et. al (Vincent, S. P., Mioskowski, C., and Lebeau, L., Nucleosides and Nucleotides, 18, 2127-2139, 1999).

Methylation of adenosine, 2'-deoxyadenosine, 2'-deoxyguanosine, inosine and xanthosine have been reported by Jones and Robins (Jones, J. W., and Robins, R. K., J. Am. Chem. Soc. 85, 193-201, 1963).

It has been found that the above mentioned alkylated derivatives undergo facile transformation such as Dimroth rearrangement, in which the methyl group is transferred from one nitrogen to a neighboring one. Thus, it has been reported that N'-methyl-2'-deoxyadenosine undergoes conversion into $N^6$-methyl-2'-deoxyadenosine in 25% aq. ammonia with a half life of 36 hrs. In another study it was found that $N^1$-methyl adenosine was stable for 3 days in 2M methanolic ammonia at room temperature and in 6 days time was totally converted into $N^6$-methyl adenosine (Mikhailov, S. N., Rozensski, J., Efimtseva, E. V., Busson, R., Aershot, A. V., and Herdewijn, P., Nucleic Acid Res 30, 1124-1131, 2002; Maca, J. B., and Wolfender R., Biochemistry, 38, 13338-13346, 1968; Jones, J. W. and Robins, R. K., J. Am. Chem Soc, 85, 193-201, 1963). We found substantial migration of methyl group from $N^1$ to $N^6$ in the presence of 2M methanolic ammonia.

This instability of the molecule prevents their use for development of alkylated nucleosides and nucleotides.

Incorporation of N1-methyl adenosine into synthetic RNA oligonucleotides has been recently carried out in which the base moiety of N1-methyl adenosine was protected with chloroacetyl group at N6 position (Mikhailov, S. N., Rozensski, J., Efimtseva, E. V., Busson, R., Aerschot, A. V., and Herdewijn, P., Nucleic Acid Res 30, 1124-1131, 2002); subsequently, use of the same protecting group i.e. chloroacetyl, was reported for the preparation of N6-chloroacetyl-N1-methyl-riboadenosine by the same group (Efimtseva, E. V., Mikhailov S. N., Rozenski, J., Busson, van Aerschot, R. A. and Herdewijn., P. Poster No. P-156, 15th International Round Table Conference, Nucleosides, Nucleotides and Nucleic Acids, 10-14 September, 2002, Leuven, Belgium.

Efimtseva et al. also reported in the above mentioned Conference that the presence of $N^1$-methyl adenosine in RNA destabilizes a duplex of RNA.

In order to study the effect of enzymes on dealkylation, it is important to synthesize well characterized alkylated nucleosides and nucleotides. Further, it has been observed that the introduction of a modified chloroacetyl protected base improves stability of a hairpin loop in RNA. Since these are important biochemical properties and bear strong implication of structure, function studies, it is important to ensure that correct and desired DNA and RNA are synthesized which are free from impurities, the side reaction products. Thus, development of nucleosides with specific protecting groups that prevent migration of the alkyl substituent in nucleosides during synthesis of desired oligonucleotides and oligodeoxynucleotides, has been carried out which forms the basis of the present invention.

Prior to utilize the N6 chloroacetyl protected N-1methyl-2'-deoxyadenosine 3'-cyanoethyl phosphoramidite, we carried out a number of kinetic studies for the deprotection of chloroacetyl group and determination of presence of any N-6 methyl-2'-deoxy adenosine, Dimroth rearrangement product, and surprisingly we observed N-6 methyl-2'-deoxy adenosine formation to the extent of 8-10%. Our subsequent studies to develop a ideal group which would be cleanly removed under aq. ammonia deprotection condition and would have negligible amount of Dimroth rearrangement product as bye product. N-6 FMOC N-1 merthyl-2'-deoxy adenosine-5'-DMT-3'-cyanoethylphosphoramidite emerged as best reagent with aq. ammonia deprotection taking place very cleanly, and the presence of N-6 methyl-2'-deoxy adenosine was found to be less than 1%.

SUMMARY OF THE INVENTION

This invention relates to preparation of synthetic nucleosides as useful substrate for oxidative dealkylation studies in relation to reversal of cytotoxic and mutagenic DNA damage. The synthetic nucleosides are N-alkylated pyrimidines and purines with appropriate nucleobase and sugar protection and the corresponding phosphoramidites, which also permit preparation of N-alkylated oligonucleotides and oligodeoxynucleotides for the study of reversal of DNA base mutagenesis.

The present invention aims at appropriately protected nucleosides and oligonucleotides that can be selectively N-alkylated to produce corresponding n-alkylated nucleosides which could be converted into phosphoramidites. The N1-alkylated purine and N-3 alkylated pyrimidines with appropriate nucleobase amino protection and 5'-DMT protection were converted back to nucleobase n-deprotected nucleosides using mild deprotection conditions, and determined to be pure N-alkylated-5'-DMT nucleosides without amino protecting group. Subsequent to this study, the novel N-alkylated-5'-DMT-n-protected nucleoside 3'-phosphoramidites were synthesized, which produce defined sequence oligonucleotides. With such types of monomers, the synthetic fully protected oligonucleotides and oligodeoxynucleotides can then be deprotected under specific deprotection conditions, without migration of the alkyl substituent. Such oligonucleotides having n-alkylated bases at defined position can serve as reagents for study of reversal of cytotoxic and mutagenic damage of DNA. Accordingly, the present invention relates to the preparation of novel pyrimidine and purine nucleosides and deoxynucleosides of Formula I, Formula 2 and Formula III.

Protected-(N-Alkylated Nucleoside)-OR'        Formula I wherein, the n-alkylated base is a methylated, ethylated, higher homolog of natural or modified DNA base, the sugar residue could be a natural ribose, a deoxyribose or a derivative thereof, OR' could represents H, a protecting group, a phosphate bond $(P(=O)(OH)_2$ or a phosphoramidite (P—N"R'"—CH2CH2CN); (P—NR"R""—OR""), at 3' or 5'-position of the sugar unit and specifically include compounds of Formula II to VIII.

BRIEF DESCRIPTION OF THE DRAWINGS

FIG. 1. $N^3$-Ethyl-5'-O-DMT-$N^4$-Bz-2'-deoxycytidine, UV spectrum graph.

FIG. 2. $N^3$-Ethyl-5'-O-DMT-$N^4$-Bz-2'-deoxycytidine, HPLC tracing.

FIG. 3. $N^3$-Ethyl-5'-O-DMT-$N^4$-Bz-2'-deoxycytidine-3'-cyanoethyl Phosphoramidite, HPLC tracing.

FIG. 4. $N^3$-Ethyl-5'-O-DMT-$N^4$-Bz-2'-deoxycytidine-3'-cyanoethylphosphoramidite, UV spectral graph.

FIG. 5. 5'-O-DMT-$N^6$—PAC—N'-Methyl-Deoxyadenosine, HPLC tracing.

FIG. 6. 5'-O-DMT-$N^6$—PAC—$N^1$-Methyl-Deoxyadenosine-3'-cyanoethylphosphoramidite; HPLC tracing.

FIG. 7. 5'-O-DMT-$N^1$-methyl-$N^6$—FMOC-2'-deoxyadenosine; Kinetic Test for FMOC Deprotection (20% methanolic ammonia at 37 C. Note: The $N^6$-methyl migration product is seen 2.27% after complete deprotection).

FIG. 8. HPLC Coinjection of 5'-O-DMT-$N^1$methyl-2'-deoxyadenosine and 5'-O-DMT-$N^6$-methyl-2'-deoxyadenosine. Note: The retention time difference of 0.553 minutes is observed. The N' methyl compound elutes slightly faster.

FIG. 9. N'-Methyl-$N^2$-DMF-Deoxyguanosine; UV Spectral graph.

FIG. 10. N'-Methyl-$N^2$-DMF-Deoxyguanosine; HPLC data.

FIG. 11. 5'-O-DMT-$N^1$-Methyl-$N^2$-DMF-Deoxyguanosine; UV Spectral graph.

FIG. 12. 5'-O-DMT-$N^1$-Methyl-$N^2$-DMF-Deoxyguanosine; HPLC data.

FIG. 13. 5'-O-DMT-$N^1$-Methyl-$N^2$-DMF-Deoxyguanosine-cyanoethylphosphoramidite; UV Spectral graph.

FIG. 14. 5'-O-DMT-$N^1$-Methyl-$N^2$-DMF-Deoxyguanosine-cyanoethylphosphoramidite; HPLC data.

DETAILED DESCRIPTION OF THE INVENTION

This invention relates to compounds of Formula 1 which specifically includes compounds represented by Formulae II to IX;

Formula II is

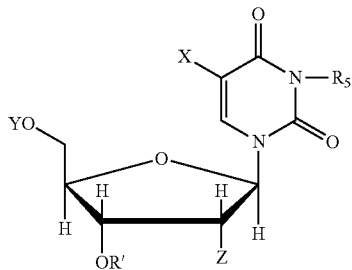
Formula II

Formula III is

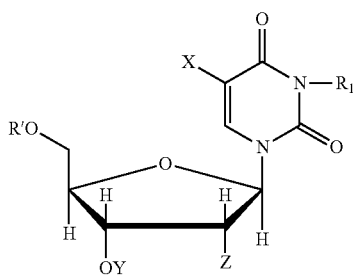
Formula III wherein, $R_1$ is an alkyl such as methyl, ethyl, X is H, a lower alkyl containing 1 to 6 carbon atoms, such as $CH_3$, $C_2H_5$, n-$C_3H_7$, etc., a branched chain lower alkyl such as iso-$C_3H_7$, iso-$C_4H_9$, t-$C_4H_9$ etc., 5-aza, halogen (F, Cl, Br, I), propyne, Z is H or $OCH_3$, F, protected $NH_2$ group, tbdsilyl protecting group, tetrahydropyranyl protecting or likewise groups. Y could be H, a protecting group such as MMT (monomethoxytrityl), DMT (dimethoxytrityl), TMT (trimethoxytrityl), FMOC (9-fluorenylmethyloxy carbonyl), tetrahydropyranyl, benzoyl, phenoxyacetyl, acetyl, propyl, butyryl, isobutyryl, or other higher homologs. The common group substitution of benzoyl group could be alkyl or halogen groups. The common substitution of phenoxy acetyl group or appropriately protected phenoxyacetyl group could be lower alkyl, lower alkoxy, nitro, halogen (F, Cl, Br, I). The substitution at 3' position, R', could be a phosphate residue (—P(=O)(OH)$_2$), a thio phosphate (—P(=S)(OH)$_2$), a phosphoramidite such as P—N($R_2$, $R_3$)(OCH$_2$CH$_2$CN), P—N($R_2$, $R_3$)(O$R_4$) wherein $R_2$, $R_3$ could be diisopropyl, diethyl, dimethyl, morpholino, pyrrolidino, and R4 is a lower alkyl containing 1-6 carbon atoms such as $CH_3$, $C_2H_5$, n-$C_3H_7$, iso-$C_3H_7$, t-$C_4H_9$.

Formula IV is

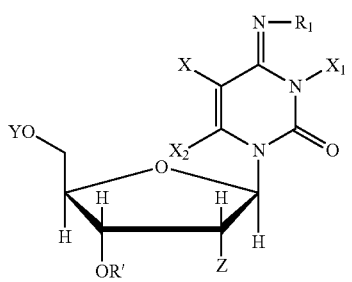
Formula IV

Formula V is

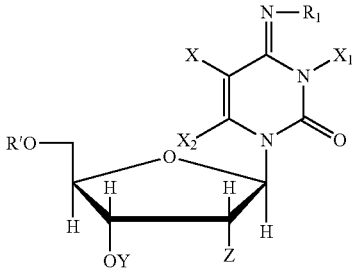
Formula V wherein, $R_1$ is benzoyl, acetyl, phenoxyacetyl, substituted phenoxyacetyl isobutyryl, 9-FMOC, dialkylformamidine and likewise base protecting groups for n-alkyl cytosine moiety. X, $X_1$, Z, and Y are as defined in Formula II, III, IV and V. $X_1$, $X_2$ could be individually a substituent, same or different, as defined for X. Y and R' are defined in formula II and III.

A purine derivative as shown in Formula VI

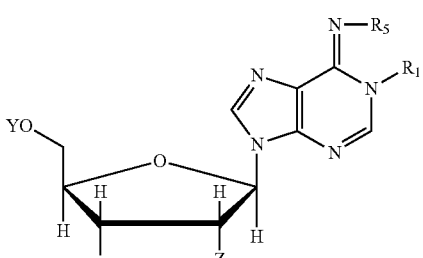
Formula VI

Formula VII is

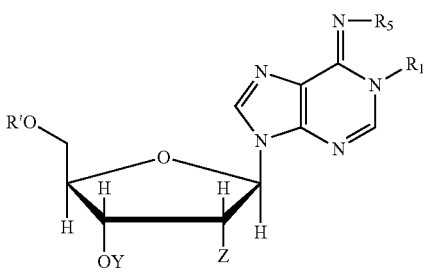
Formula VII wherein, $R_1$ has been defined in formula IV and V; Y, Z are as defined in Formula II, III, IV and V. $R_5$ is a protecting group such as, phenoxy acetyl, protected phenoxy acetyl, pivaloyl, 9-FMOC group, an imine derivative such as formamidine, dimethylformamidine. A purine modification could be, but not limited to, 7-deazaadenine, 7-iodo-7-deazaadenine, 7-propyne-7-deaza adenine.

A purine derivative as shown in Formula VIII,

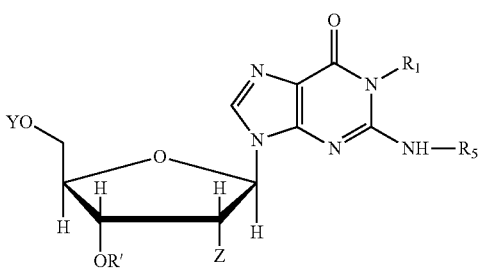
Formula VIII

A purine derivative as shown in Formula IX,

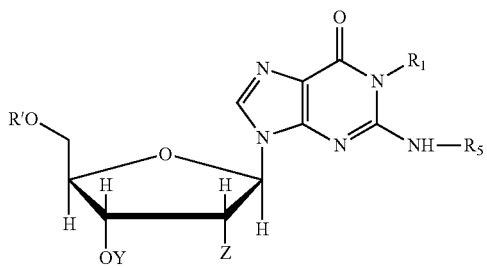

Formula IX wherein, $R_1$, $R_5$, are defined in formula VI and VII, Z and Y, are as defined in Formula II-VII, a purine modification could be, but not limited to, 7-deazaguanine, 7-iodo-7-deazaguanine, 7-propyne-7-deazaguanine.

Preferred Compounds of the invention are:
1. $N^1$-Methyl-$N^6$—PAC-deoxyadenosine (1)
2. 5'-O-DMT-$N^6$—PAC-$N^1$-Methyl-deoxyadenosine (2)
3. 5'-O-DMT-$N^6$—PAC-$N^1$-Methyl-deoxyadenosine-3'-cyanoethyl phosphoramidite (3)
4. $N^1$-Methyl-$N^2$-DMF-deoxyguanosine (4)
5. 5'-O-DMT-$N^1$-Methyl-$N^2$-DMF-deoxyguanosine (5)
6. 5'-O-DMT-$N^1$-Methyl-$N^2$-DMF-deoxyguanosine-3'-cyanoethyl Phosphoramidite (6)
7. $N^3$-Ethyl-5'-O-DMT-$N^4$-Bz-2'-deoxycytidine (7)
8. $N^3$-Ethyl-5'-O-DMT-$N^4$-Bz-2'-deoxycytidine-3'-N,N-diisopropyl cyanoethyl phosphoramidite (8)
9. $N^1$-Methyl-$N^6$—FMOC-2'-deoxyadenosine (9)
10. 5'-DMT-$N^1$-Methyl-$N^6$—FMOC-2'-deoxyadenosine (10)
11. 5'-DMT-$N^1$-Methyl-$N^6$—FMOC-2'-deoxyadenosine-3'-cyanoethyl,n,n-diisopropyl phosphoramidite (11).

EXPERIMENTAL EXAMPLES

Preparation of $N^1$-Methyl-$N^6$-Phenoxy acetyl-Deoxyadenosine (1)

$N^1$-Methyl deoxy adenosine (made by adding methyl iodide in dimethyl acetamide solution of dA and stirring at room temp. for 18 hours) (J. W. Jones and R. K. Robins, J. Am. Chem Soc, 85, 193-201, 1963). 18.8 mmole was taken in dry pyridine 50 ml and the solution was cooled to 0° C. and 75.5 mmole trimethyl chloro silane was added dropwise under argon. Reaction mixture was brought to 30° C. and stirred for half an hour. Reaction mixture was cooled to 0° C. and 37.5 mmole phenoxy acetyl chloride was added drop wise under argon and stirred at 30° C. for 2.5 hours. Reaction was cooled again to 0° C. and 10 ml distilled water was added and stirred for 10 minutes then 5 ml pre-cooled ammonium hydroxide solution (28%) was added at 0° C. and stirred for 2 minutes. The solution was then evaporated under high vacuum to gum. The gum was then taken in chloroform and extracted twice with water. The organic layer was dried on sodium sulfate and evaporated to gum. TLC of this compound showed two major spots, lower spot was found to be the right spot. The residue was then purified on silica gel column using chloroform and a gradient system containing 5-10% methanol in chloroform. The pure product was pooled and dried. The yield was approx. 25%. TLC $R_f$ of compound 1, 0.45 in chloroform:methanol 92:8, HPLC analysis showed single peak 92% $R_t$ 5.1 min (90:10 0.1 M TEAA, pH 7.5:acetonitrile; C-18 Reverse phase column, system A: TEAA:triethylammonium acetate). UV (methanol) λ max (nm) 299 (ε 12,928) ratio 250/260; 0.666, 260/280; 0.631.

$^1$H NMR (CD$_3$OD): 8.31 (s, 2, H2 & H8), 6.76-7.22 (1d & 2m, 5, O—C$_6$H$_5$), 6.39-6.42 (t, 1, H1'), 4.91 (s, 2, CH$_2$—O-Phenyl), 4.53-4.55 (m, 1, H3'), 4.01-4.03 (m, 1, H4'), 3.70-3.81 (2q, 2, H5' & H5"), 3.41 (s, 3, N—CH$_3$), 2.41-2.73 (2m, 2, H2' & H2")

Preparation of 5'-O-DMT-$N^6$—PAC-$N^1$-Methyl-Deoxyadenosine (2)

Compound 1 (3.75 mmole) was dried with pyridine then taken in 15 ml pyridine, the solution was cooled to 0° C. and to the stirred solution 4.5 mmole DMT-CI was added. Reaction mixture was brought to room temp. and stirred for 2 hours. Then reaction was quenched with pre-cooled methanol at 0° C. The solution was then evaporated under high vacuum to gum. The gum was then taken in chloroform and extracted with 5% aqueous sodium bicarbonate solution and then with saturated brine solution. The organic layer was dried on sodium sulfate and evaporated to gum. TLC of this compound showed one major spot. Compound was then purified on silica gel column using chloroform and a gradient system containing 2-5% methanol in chloroform. The pure product was pooled and dried. The yield was approx. 65%. TLC $R_f$ of compound 2, 0.28 in chloroform-methanol (96:4), HPLC analysis showed single peak 98.3% $R_t$ 7.68 min (40:60:0.1 M TEAA:acetonitrile; system B). UV (methanol) λ max nm) 277.5 (ε 13,175) ratio 250/260; 1.109, 260/280; 0.616.

$^1$H NMR (CD$_3$OD): 8.17 (s, 1, H8), 8.12 (s, 1, H2), 6.73-7.39 (m, 18, aromatic), 6.38-6.41 (t, 1, H1'), 4.90 (s, 2, CH$_2$—O-Phenyl), 4.58-4.59 (m, 1, H3'), 4.13-4.14 (m, 1, H4'), 3.74-3.75 (ds, 6, OCH$_3$), 3.39 (s, 3, N—CH$_3$), 3.27-3.37 (2q, 2, H5' & H5"), 2.47-2.88 (2m, 2, H2' & H2").

Preparation of 5'-O-DMT-$N^6$—PAC-$N^1$-Methyl-Deoxyadenosine-3'-cyanoethyl phosphoramidite (3)

Compound 2 (1.42 mmole) was thoroughly dried with dry acetonitrile and taken up in dry tetrahydrofuran. To the stirred solution was added N,N-diisopropyl ethylamine (2.84 mole) under argon, the solution maintained at 5° C. To this solution was added drop wise N,N-diisopropylamino cyanoethyl phosphoramidic chloride (1.56 mmole), followed by further reaction at 25° C. for additional one hour. The reaction mixture was diluted with ethyl acetate and washed with saturated aqueous sodium bicarbonate once, followed by saturated sodium chloride once. The organic layer was dried over anhydrous sodium sulfate, followed by evaporation under vacuum. The residue was purified by column chromatography. Yield of the pure product was 78%. The solvent system for column and TLC was ethyl acetate:acetone and triethylamine in a ratio of 90:9:1. The TLC $R_f$ of compound 0.5 & 0.59, HPLC analysis showed sharp doublets 99.2%, $R_t$ 3.43 min & 3.69 min (95:5:::acetonitrile: 0.1 M TEAA; system C), UV (methanol). λ max (nm) 278 (ε 12,334) ratio 250/260; 1.099, 260/280; 0.618.

$^1$H NMR (CDCl$_3$): 7.87-7.89 (d, 1, H2), 7.74 (s, 1, H8), 6.77-7.43 (m, 18, aromatic), 6.29-6.31 (t, 1, H1'), 4.93 (s, 2, CH$_2$—O-phenyl), 4.68-4.69 (m, 1, H3'), 4.27-4.29 (m, 1, H4'), 3.77-3.83 (m, 1, POCH$_2$), 3.77 (ds, 6, OCH$_3$), 3.73-3.75 (m, 1, POCH$_2$), 3.55-3.69 (dm, 2, H5' & H5"), 3.29-

3.37 (m, 2, (Me$_2$CH)$_2$N), 2.44-2.62 (dt, 2, CH$_2$CN), 1.15-1.19 (m, 12, [(CH$_3$)$_2$C]$_2$N). $^{31}$P NMR (CDCl$_3$) δ 149.392, 149.489, J 0.097.

Preparation of N'-Methyl-N$^2$-DMF-Deoxyguanosine (4)

N$^2$-DMF-dG (made by regular procedure using dG solution in dimethyl formamide and adding dimethyl formamidine dimethyl acetal and continuing the reaction for 48 hours followed by crystallization) 12.4 mmole was taken in 40 ml dimethyl formamide. The solution was cooled to 0° C. and then 13.65 mmole sodium hydride was added under argon and reaction was stirred for an hour then 13.65 mmole methyl iodide was added at 0° C. and let the reaction proceed at the same temperature for three hours. Reaction became thick solid; 100 ml ether was added and solid was filtered through Buchner funnel and washed twice with ether:water (90:10). Solid was dried on high vacuum. The yield was approx. 65%. TLC R$_f$ of compound 4, 0.5 in chloroform:methanol 85:15, HPLC analysis showed single peak 96% R$_t$ 1 2.62 min (80:20::0.1 MTEAA:Acetonitrile:system D). UV (0.2N HCl) λ max (nm) 296 (ε 21,265) ratio 250/260; 1.289, 260/280; 0.412.

$^1$H NMR (DMSO): 8.56 (s, 1, N=CH—N), 8.04 (s, 1, H8), 6.24-6.26 (t, 1, H1'), 5.30 (s, 1, 5'OH), 4.92 (s, 1, 3'OH), 4.37-4.38 (m, 1, H3'), 3.81-3.84 (m, 1, H4'), 3.51-3.56 (2q, 2, H5' & H5"), 3.32 (s, 3, N—CH$_3$), 3.08 & 3.19 (ds, 6, N(CH$_3$)$_2$), 2.21-2.24 & 2.5-2.62 (2m, 2, H2' & H2").

Preparation of 5'-O-DMT-N1-Methyl-N$^2$-DMF-Deoxyguanosine (5)

Compound 4 (8.3 mmole) was dried with pyridine then taken in 30 ml of pyridine, the solution was cooled to 0° C. and to the stirred solution 10 mmole DMT-Cl was added. Reaction mixture was brought to the room temperature and stirred for two hrs. Then reaction was quenched with pre-cooled methanol at 0° C.; the solution was then evaporated under high vacuum to gum. The gum was then taken in chloroform and extracted with 5% aq. sodium bicarbonate solution and then with saturated brine solution. The organic layer was dried on sodium sulfate and evaporated to gum. TLC of this compound showed one major spot. Compound was then purified on silica gel column using chloroform:hexane:acetone 50:30:20 containing 8% methanol. The pure product was pooled and dried. The yield was approx. 56%. TLC R$_a$ of compound 5, 0.27 in chloroform:hexane:acetone 50:30:20 containing 2% methanol. HPLC analysis showed single peak 99% R$_t$ 4.41 min (system B). UV (methanol) λ max (nm) 307 (ε 17,676) ratio 250/260; 1.678, 260 I 280; 0.584.

$^1$H NMR (CD$_3$CN): 8.50 (s, 1, N=CH N), 7.66 (s, 1, H8), 6.77-7.38 (3m, 13, Aroma), 6.26-6.28 (t, 1, H1'), 4.53-4.54 (m, 1, H3'), 3.98 (m, 1, H4'), 3.74 (s, 6, OCH$_3$), 3.55 (s, 3, N—CH$_3$) 3.17-3.27 (2q, 2, HS' & H5"), 3.10 & 3.11 (ds, 6, N(CH$_3$)$_2$), 2.34-2.37 & 2.74-2.77 (2m, 2, H2' & H2").

Preparation of 5'-O-DMT-N$^1$-Methyl-N$^2$-DMF-Deoxyguanosine-3'-Cyanoethyl Phosphoramidite (6)

Compound 5 (3.13 mmole) was thoroughly dried with dry acetonitrile and taken up in 20 ml dry tetrahydrofuran. To the stirred solution was added N,N-diisopropyl ethylamine (6.26 mmole) under argon; the solution maintained at 5° C. To this solution was added drop wise N,N-diisopropylamino cyanoethyl phosphoramidite chloride (3.4 mmole), followed by further reaction at 25° C. for additional one hour. The reaction mixture was diluted with ethyl acetate and washed with saturated aq. sodium bicarbonate once, followed by saturated sodium chloride once. The organic layer was dried over anhydrous sodium sulfate, followed by evaporation under vacuum. The residue was purified by column chromatography. Pure fractions were pooled and dried. Yield of the pure product was 60%. The solvent system for column and TLC was chloroform:hexane and triethylamine in a ratio of 70:20:10. The TLC R$_f$ of compound VI, 0.46 & 0.62, HPLC analysis showed sharp doublets 95.5%, R$_t$ 3.46 min & 3.53 min (90:10::acetonitrile:0.1 M TEAA; system E), UV (methanol) λ max (nm) 307 (ε 16,371) ratio 250/260:1.738; 260/280:0.617.

$^1$H NMR (CDCl$_3$): 8.52-8.53 (d, 1, N—CH—N), 7.70-7.71 (d, 1, H8), 6.77-7.41 (tm, 13, Ar), 6.36-6.37 (m1, H1), 4.63-4.71 (m, 1, H3'), 4.24-4.25 (m, 1, H4'), 3.77 (ds, 6, OCH$_3$), 3.57-3.67 (m, 2, H5' & H5"), 3.28-3.32 (m, 4, (Me$_2$CH)$_2$N & POCH$_2$), 3.12-3.18 (dd, 6, N—(CH$_3$)$_2$), 2.46-2.63 (dm, 4, CH$_2$CN, H2', & H2"), 1.15-1.19 (m, 12, ((CH$_3$)$_2$C)$_2$N). $^{31}$P NMR (CDCl$_3$) δ 149.256-149.392, J 0.136.

Preparation of N$^3$-Ethyl-5'-O-DMT-N$^4$-Bz-2'-Deoxycytidine (7)

DMTdBzC (7.0 gm) was taken in dimethylacetamidite (21 ml). To the solution was added ethyliodide (7.0 ml), stirred for 6 hrs at room temperature, and then diisopropylethylamine (1.79 ml) was added. The sealed reaction mixture was kept at 37° C. for over night and then poured in to 10% aq. sodium bicarbonate. The oil was separated, taken in chloroform, and washed with brine and passed through anhydrous sodium sulfate and evaporated. TLC system was 50:30:20:1 (chloform:hexane:acetone:methanol; System F). The crude mixture was purified by column chromatography on silica gel (70-230 mesh) using a solvent system consisting of dichloromethane:hexane:acetone::50:30:20. The title compound (1.4 gm) was obtained in pure form. TLC in system F, R$_f$ 0.63. HPLC in 95:5::acetonitrile:0.1 M TEAA pH 7.5), reverse phase, retention time; 2.97 minutes. UV (methanol), ratio 250/260; 1.529; 260/280; 0.984; Emax at 250 nm; 13721.

Preparation of N$^3$-Ethyl-5'-O-DMT-N$^4$-Bz-2'-Deoxycytidine-3'-N,N-Diisopropyl Cyanoethyl Phosphoramidite (8)

To a mixture of N$^3$-ethyl-5'-O-DMT-N$^4$-Bz-2'-deoxycytidine (1.0 gm) taken in anhydrous THF (10 ml) and diisopropylethylamine (0.52 ml, 2 eq), N,N-diisopropyl-cyanoethylphosphonamidic chloride reagent (0.37 gm; 1.1 eq) was added drop wise at zero degrees. The reaction time was 1 hour. The tic was checked in 60:30:10::hexane:chloroform:triethylamine. The reaction mixture was worked up following standard procedure. The crude product was purified on silica gel column (70-230 mesh), column length 12 inches, column diameter 1.0 inch. The column chromatography system was 30:60:10::ethyl acetate:hexane:triethylamine. Title compound (600 mg) was obtained in pure form with only trace of PV peak. TLC system was 30:60:10::ethyacetate:hexane:triethylamine; R$_f$ 0.50. HPLC, (95:5::acetonitrile:0.1 M TEAA pH 7.5); doublet; retention time; 5.51 and 5.701, UV (methanol); 250/260; 1.505, 260/280; 0.960, Emax at 250 nm; 16343.

Preparation of N'-Methyl-dA (9)

Reported by J. W. Jones and R. K. Robins, J. Am. Chem. Soc., 85, 193-201, (1963).

2'-Deoxy adenosine (1.0 gm) was taken in dimethylacetamide (3.0 ml), followed by addition of methyliodide (1.0 ml). The reaction mixture was sealed and stirred for 18 hours at room temperature. Deoxyadenosine slowly dissolved and a product slowly precipitated out. After 18 hours reaction, acetone (15 ml) was added, and stirring continued for 30 minutes. The solid was filtered and washed with acetone. TLC was run in several systems, (a) Chl:methanol::92:8, (b) 75:25::Chl:methanol (c) in 5% aq. ammonium bicarbonate (d) isopropyl alcohol:ammonium bicarbonate::65:35). A repeat preparation of $N^1$-Methyl dA, the quantities were dA (10 gm), dimethylacetamidite (30 ml), methyliodide (10 ml). The sealed reaction mixture stirred overnight, followed by addition of acetone (100 ml). The solid was filtered and washed with additional acetone. Quantity obtained; 7 gm.

Preparation of $N^1$-Methyl-$N^6$—FMOC-2'-Deoxyadenosine (10)

$N^1$-Methyl-2'-deoxy adenosine hydroiodide salt (2.5 gm) was taken in pyridine (25 ml). The solution was cooled to 0° C. From pressure equalizing funnel was added chlorotrimethylsilane (2.42 ml; 3 eq) drop wise. The reaction mixture was then brought to room temperature and stirred for 45 minutes at room temperature, followed by addition of fluoreriylcarbonyl chloride (FMOC Chloride) (1.96 gm; 1.2 eq) through pressure equalizing funnel slowly. The reaction mixture was stirred at RT for 2.5 hours. The reaction mixture was brought to zero degrees, and water (5.0 ml) was added and the mixture stirred for 10 minutes at zero degrees. This was followed by addition of aq ammonia (3.97 ml), and the mixture was stirred for 1.0 minute. The reaction mixture was then pumped out. TLC run in chloroform:methanol::90:10. Column chromatography of the above 2.5 gm batch; Column length 14 inches, column diameter 2 inch, solvent system: chloroform-methanol (100 to 90% chloroform gradient) Quantity of pure product obtained; 2.5 gm.

Preparation of 5'-O-DMT-$N^1$-Methyl-N6-FMOC-2'-Deoxyadenosine 3'-Cyanoethylphosphoramidite (11)

To a mixture of 5'-O-DMT-$N^1$-methyl-N6-FMOC-2'-deoxyadenosine (2;0 gm) taken in anhydrous THF (20 ml) and diisopropylethylamine (0.88 ml, 2 eq), N,N-diisopropylcyanoethylphosphonamidic chloride reagent (0.62 ml 1.1 eq) was added drop wise at zero degrees. The reaction was then allowed to proceed at room temperature for 1 hour. The tic was checked in 90:10:1::ethylacetate:acetone:triethylamine. The reaction mixture was worked up following standard procedure. The crude product was purified on silica gel column (70-230 mesh}, column length 12 inches, column diameter 1.5 inches. The column chromatography system was 90:10:1::ethyl acetate:acetone:triethylamine. Title compound (1.6 gm) was obtained in pure form with less than 2% of PV peak. TLC system was 90:10:1::ethylacetate:acetone: triethylamine; $R_f$ 0.60. UV (methanol); 250/260; 0.757; 260/280; 1.326, Emax; at 266 nm 17408. HPLC (system 90:10::acetonitrile: 0.1 M triethylammonium acetate, pH 7.5) retention time; 7.31 and 8.18 minutes. $^{31}$P NMR (CDCl$_3$); 149.531 and 149.400.

Chemical Studies and Discussion

In the guanine series, position of methyl group on $N^1$ was confirmed by comparing with $^1$H NMR of known sample of $N^2$-Me-dG. It was confirmed by TLC & HPLC that migration of methyl group from $N^1$ position to $N^2$ position of the ring does not take place in the case of Guanosine during 24 hours ammonia reaction to knock off N-DMF group.

In the adenine series, it was found that during 20% methanolic ammonia hydrolysis of N-PAC protecting group, approx. 5-6% $N^1$ methyl migrated to $N^6$ position on exocyclic amine in 18 hours at 37 C (required to knock off Phenoxy acetyl from $N^6$ position). To minimize this migration, we introduced N-FMOC group in place of N-PAC which reduced 20% methanolic ammonia hydrolysis time to only 4 hours at 37° C. but even in 4 hours, approx. 2.5% migration took place. This migration of methyl group from $N^1$ to $N^6$ position was confirmed by TLC & HPLC. The migration of N-chloroacetyl group as published by was found to be approx. 9-10%.

What is claimed is:
1. A nucleoside of the formula (IV),

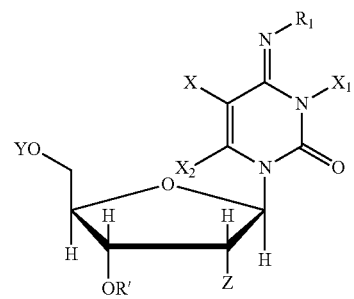

Formula (IV)

wherein,
$R_1$ is phenoxyacetyl, substituted phenoxyacetyl, or 9-fluorenylmethoxycarbonyl (9-FMOC);
X is hydrogen, a lower alkyl containing 1 to 6 carbon atoms, or a branched chain lower alkyl;
$X_1$ is methyl, or ethyl;
$X_2$ is a hydrogen atom, a lower alkyl containing 1 to 6 carbon atoms, or a branched chain lower alkyl;
Y is monomethoxytrityl, dimethoxytrityl, trimethoxytrityl, or tetrahydropyranyl;
R' is a phosphoramidite, said phosphoramidite is P—N($R_2$,$R_3$)(OCH$_2$CH$_2$CN) or P—N($R_2$,$R_3$)(OR$_4$), wherein $R_2$ and $R_3$ are selected from the group consisting of diisopropyl, diethyl, dimethyl, morpholino, and pyrrolidino; and $R_4$ is a lower alkyl containing 1-6 carbon atoms; and
Z is hydrogen, fluoro, or protected amino.

* * * * *